United States Patent
Palushi et al.

(10) Patent No.: US 10,271,871 B2
(45) Date of Patent: Apr. 30, 2019

(54) MULTI-WINDOW SURGICAL CUTTING APPARATUS

(71) Applicant: Acclarent, Inc., Irvine, CA (US)

(72) Inventors: Jetmir Palushi, Irvine, CA (US); Lauren Radtke, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 27 days.

(21) Appl. No.: 15/298,903

(22) Filed: Oct. 20, 2016

(65) Prior Publication Data

US 2018/0110540 A1     Apr. 26, 2018

(51) Int. Cl.
*A61B 17/3207*     (2006.01)
*A61B 17/32*     (2006.01)

(52) U.S. Cl.
CPC ........... *A61B 17/320783* (2013.01); *A61B 17/32002* (2013.01); *A61B 17/320758* (2013.01); *A61B 2017/320032* (2013.01); *A61B 2217/005* (2013.01)

(58) Field of Classification Search
CPC ............................................. A61B 17/320783
See application file for complete search history.

(56) References Cited

U.S. PATENT DOCUMENTS

| | | | |
|---|---|---|---|
| 4,811,734 A * | 3/1989 | McGurk-Burleson | A61B 17/32002 30/240 |
| 5,084,052 A | 1/1992 | Jacobs | |
| 5,106,364 A * | 4/1992 | Hayafuji | A61B 17/32002 30/208 |
| 5,423,844 A * | 6/1995 | Miller | A61B 17/32002 600/563 |
| 5,730,752 A * | 3/1998 | Alden | A61B 17/32002 604/35 |
| 2008/0021488 A1* | 1/2008 | Berberich | A61B 17/32002 606/170 |
| 2008/0249553 A1* | 10/2008 | Gruber | A61B 17/32002 606/171 |
| 2015/0327881 A1* | 11/2015 | Willhite | A61B 17/32002 606/180 |

FOREIGN PATENT DOCUMENTS

| | | |
|---|---|---|
| EP | 0310285 A2 | 4/1989 |
| EP | 0809466 B1 | 11/2006 |
| WO | WO 2010/118172 A1 | 10/2010 |

OTHER PUBLICATIONS

International Search Report and Written Opinion dated Nov. 28, 2017 for International Application No. PCT/US2017/055692, 16 pages.

* cited by examiner

*Primary Examiner* — Richard Louis
(74) *Attorney, Agent, or Firm* — Frost Brown Todd LLC

(57) ABSTRACT

An apparatus for addressing tissue and bone in a nasal cavity includes a rotary or oscillatory cutting member disposed in the lumen of a shaft. The shaft may have a first window region oriented in first direction and a second window region oriented in a second direction. The cutting member may have a first cutting edge configured to be cyclically moved across at least a portion of the first window region and a second cutting edge configured to be cyclically moved across at least a portion of the second window region. A shield is selectively positionable to occlude the first and to occlude the second window region.

20 Claims, 6 Drawing Sheets

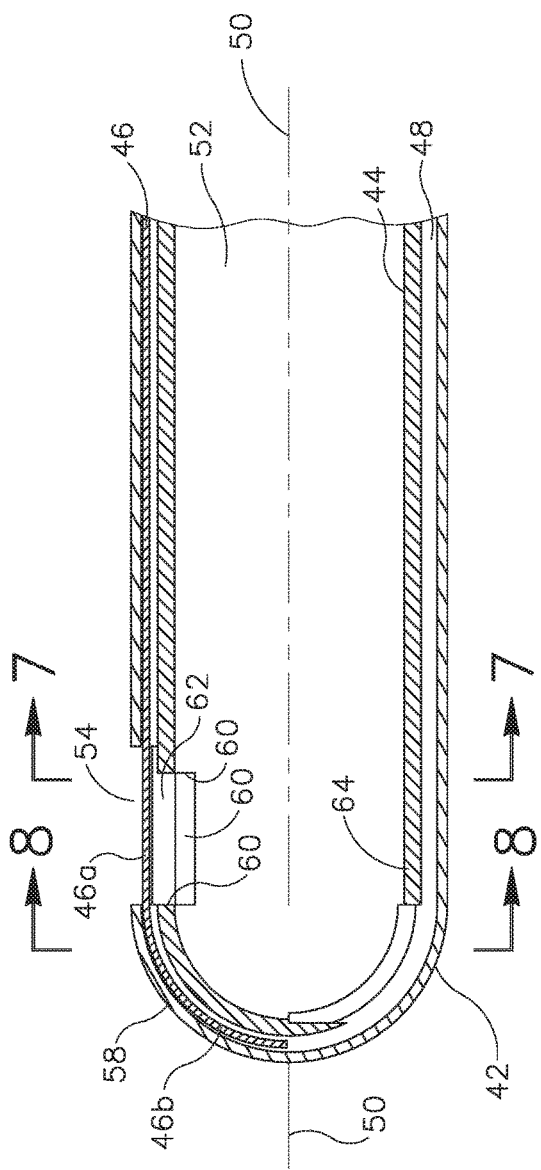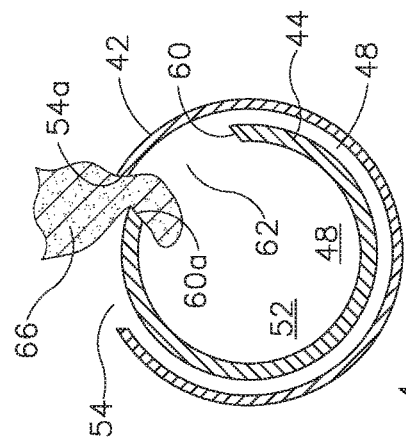

MULTI-WINDOW SURGICAL CUTTING APPARATUS

BACKGROUND

Surgical cutting instruments configured for removal of lesions, polyps and fibroids within the nasal cavity are known. Some configurations may include an elongated inner member rotatably coaxially disposed within a tubular outer tubular member. The distal end of the outer member includes an opening, and the distal end of the inner member includes cutting edges. The proximal ends of the two members may be connected to a handle directly or via a detachable hub. The inner member may be hollow and in communication with an aspiration port so that severed tissue, etc. can be aspirated out through the hollow member. The cutting edges can have any various configurations suitable for the particular type of tissue or bone cutting to be done, with the opening configured to cooperate with the specific cutting edge configuration.

To use such surgical cutting instrument to address tissue or bone, the opening/cutting edge is advanced to the target surgical site, and the opening positioned adjacent the tissue or bone to be removed. The opening may be repositioned to address tissue which was could not be accessed with the instrument in the previous position. Surgical cutting instruments with a fixed opening allow surgeons to cut only in the direction of the fixed opening cutting. To access, cut and remove tissue at various locations, surgeons have to reposition the instrument at various angles; or in some instances, change to other instruments having a more appropriately arranged opening.

It may be desirable to access, cut and remove tissue and bone at various locations without having to reposition or change the surgical instrument. While several different surgical instruments and methods of use have been made for tissue and bone removal within the nasal cavity, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a cross-sectional view taken along the midline of the distal portion of the surgical cutting instrument of FIG. 1, with the shield in a first position;

FIG. 4 depicts a cross-sectional view taken along the axis of the shaft through the first window region of the surgical cutting instrument of FIG. 1, with the shield omitted for clarity, illustrating tissue extending into the first window region;

Figure 1:
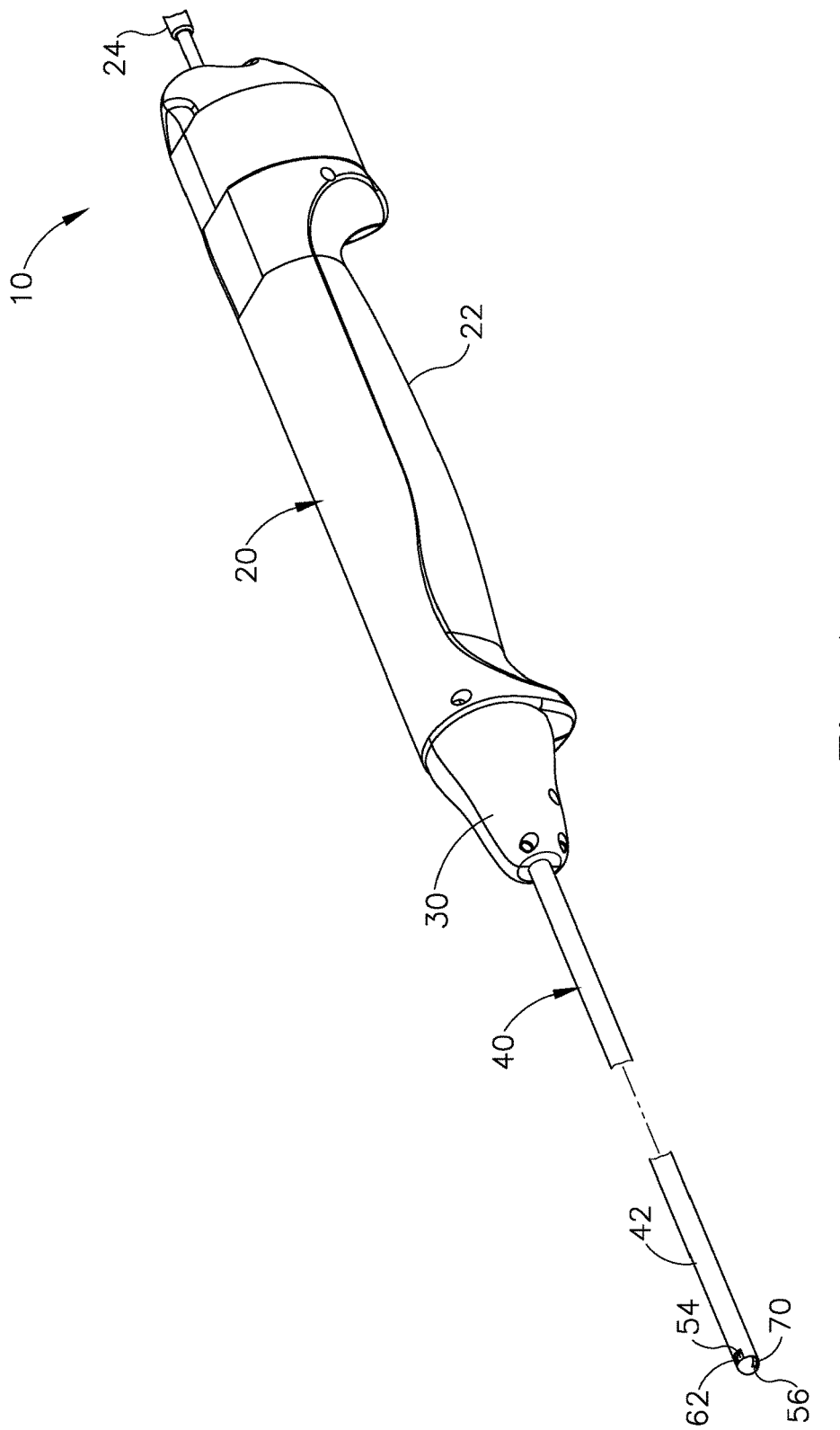
FIG. 1 depicts a perspective view of an exemplary surgical cutting instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Surgical Cutting Instrument

Figure 2:
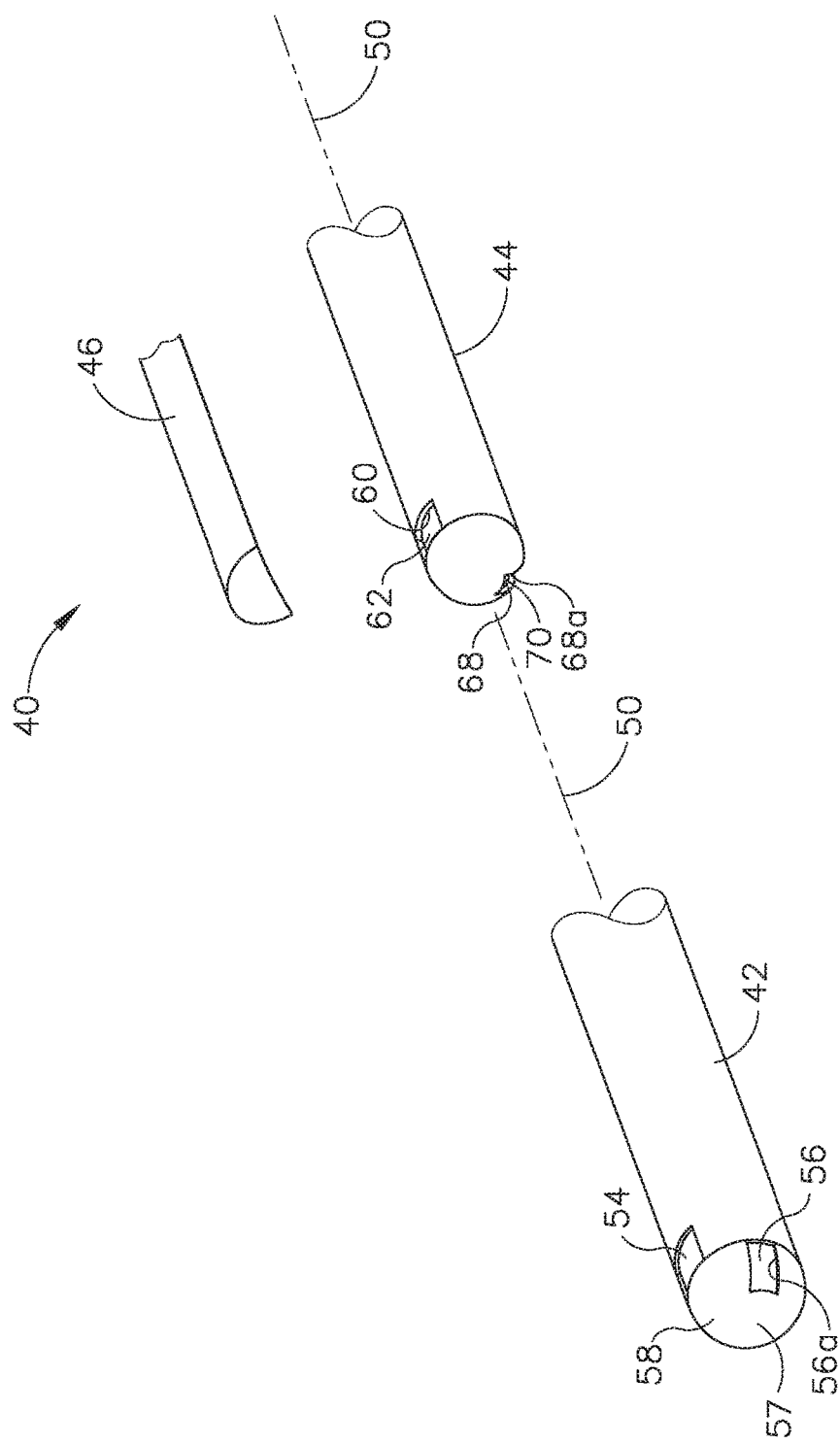
FIG. 2 depicts an exploded perspective fragmentary view of the distal portion of the surgical cutting instrument of FIG. 1.

FIGS. 1-3 show an exemplary surgical cutting instrument (10) that may be used to remove tissue and bone from the nasal cavity, as well as from any other suitable location. Surgical cutting instrument (10) of the present example comprises handle assembly (20), hub (30) and shaft assembly (40) extending distally from handle assembly (20). Handle assembly (20) includes handle (22) which may be of any suitable configuration. Handle (22) may include controls for the operation of surgical cutting instrument (10), or the controls may be located remotely. Surgical cutting instrument (10) may include suction port (24) which may be configured in any suitable manner to enable aspiration of tissue and bone from the surgical site. Rotational or oscillatory motion is delivered by handle assembly (20) to shaft assembly (40). Any suitable rotational or oscillatory motion source may be utilized, which may be housed within handle assembly (20) or which may be external and connectable to handle assembly (20). Handle assembly (20) may house a battery (not shown) or may be connected to an external power source. Handle (22) and other components of handle assembly (20) may be made of any suitable material, including for example polycarbonate.

Shaft assembly (40) comprises shaft (42), cutting member (44) and shield member (46). Shaft (42), illustrated as a tube, defines central lumen (48) which extends throughout the length of shaft assembly (40). Cutting member (44), illustrated as a tube, is disposed in lumen (48) and is configured to be rotated or oscillated about longitudinal axis (50) of shaft assembly (40) at distal portion (58). Although shaft assembly (40) is depicted as rigid, all or a portion of shaft assembly (40) may be flexible, with axis (50) comprising the series of cross-sectional centers. Cutting member (44) extends to handle assembly (20), where it is connected to a source of rotational or oscillatory power (not shown). Cutting member (44) defines lumen (52). Either or both of lumens (48) and (52) may be in fluid communication with suction port (24).

Shield member (46) is illustrated as disposed in lumen (48), interposed in the cylindraceous space between shaft (42) and cutting member (44) and shaped complementarily to the outer surface of cutting member (44) and to the inner surface of shaft (42). Shield member (46) is illustrated as being a cylindraceous sector—having a cross-section that is a curved segment, i.e., less than 360°, along most of its axial length. Shield member may be of any suitable configuration, including of an annular cross-section along all or a portion of its axial length. As described below, shield member (46) is configured to be moved between and including at least a first and a second position.

Shaft (42) includes first window region (54) and second window region (56), also referred to herein as first opening (54) and second opening (56), at distal portion (58). Distal portion (58) terminates in curved end, such as generally spherical end (57). First window region (54) and second window region (56) are respective openings through shaft (42) through which central lumen (48) is, unless occluded as described below, in fluid communication with the ambient environment surrounding shaft (42). First window region (54) is oriented toward a first direction, radially outwardly relative to longitudinal axis (50) such that tissue or bone may extend through first window region (54) into central lumen (48) in a radially inward direction when distal portion (58) is urged radially against such tissue or bone. The first direction is illustrated as comprising only a radial directional component. Second window region (56), illustrated as formed in spherical end (57), is oriented toward a second direction, axially (parallel relative to longitudinal axis (50)) such that tissue or bone may extend through second window region (56) into central lumen (48) when distal portion (58) is urged axially against such tissue or bone. It is noted that the second direction includes a radial directional component in addition to the axial directional component such that tissue or bone may extend through second window region (56) when distal portion (58) is urged radially against such tissue or bone. The second window region (56) may be located and oriented in any suitable direction, such that the second direction does not include a radial directional component or includes only a radial direction component. Shaft (42) may be made of any suitable material, such as polycarbonate.

Cutting member (44) may be made of any suitable material, such as stainless steel. Cutting member (44) includes first cutting edge (60) which defines first cutting window (62) at distal portion (64) of cutting member (44). It is noted that less than the entirety of first cutting edge (60) may be configured for cutting tissue and bone against an opposing surface. Referring also to FIG. 4, at least a portion of first cutting edge (60) is disposed to move adjacent to and across at least a portion of first window region (54) when cutting member (44) is rotated or oscillated about axis (50). FIG. 4 illustrates tissue (66) extending through first window region (54), such as would occur when distal portion (58) is urged radially against such tissue. As cutting member (44) moves in a clockwise direction, edge (54a) of first window region (54) acts as and is an opposing surface to first cutting edge portion (60a) of first cutting edge (60) whereby tissue (66) may be severed. Each of first cutting edge portion (60a) and edge (54a) may have any configuration which suitably cooperates with the other to sever tissue (66), such as a knife edge, a serrated edge, bipolar, monopolar or harmonic energy modality, or laser activated cutting edge. The extent of movement and position of first cutting edge portion (60a) relative to edge (54a) is sufficient to separate tissue (66), whether by severing, tearing or any other mechanism. For example, first cutting edge portion (60a) may cyclically move across at least a portion of first window region (54). In FIG. 4, further clockwise movement of cutting member (60) will advance cutting edge portion (60a) past edge (54a), such as results from oscillation about axis (50) or from full rotation about axis (50).

Cutting member (44) also includes second cutting edge (68) which defines second cutting window (70) at distal portion 64 of cutting member (44). It is noted that less than the entirety of second cutting edge (68) may be configured for cutting tissue and bone against an opposing surface. At least a portion of second cutting edge (68) is disposed to move adjacent to and across at least a portion of second window region (56) when cutting member (44) is rotated or oscillated about axis (50). When tissue extends through second window region (56), in a fashion similar to that depicted in FIG. 4 for first window region (54), such as would occur when distal portion (58) is urged axially against such tissue. As cutting member (44) rotates in a clockwise direction, edge (56a) of second window region (56) is an opposing surface to second cutting edge portion (68a) of second cutting edge (68) whereby tissue (66) may be severed. Each of second cutting edge portion (68a) and edge (56a) may have any configuration which suitably cooperates with the other to sever tissue (66), such as a knife edge and a serrated edge. The extent of movement and position of second cutting edge portion (68a) relative to edge (56a) is configured sufficiently to separate tissue (66), whether by severing, tearing or any other mechanism. For example, second cutting edge portion (68a) may cyclically move across at least a portion of second window region (56).

Cutting member (44) is illustrated configured as a hollow tube, but is not limited to being tubular defining its own lumen (52). Cutting member (44) may be of any suitable configuration to provide first cutting edge 60 and second cutting edge (68). For example, cutting member (44) may comprise a shaft disposed coaxial with axis (50) within lumen (48) which carries first and second cutting edges at its distal portion (64).

Figure 5:
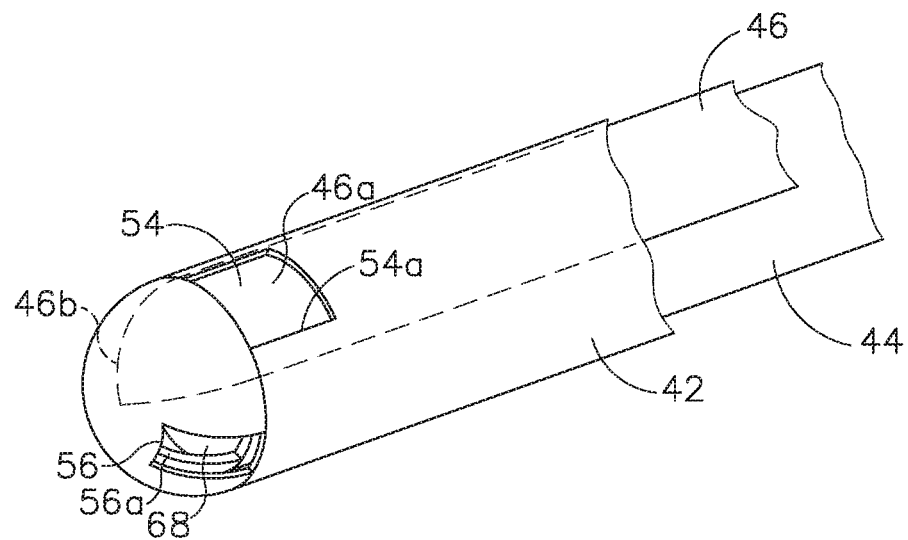
FIG. 5 depicts an enlarged perspective fragmentary view of the distal portion of the exemplary surgical cutting instrument of FIG. 1, with the shield in a first position.
Figure 6:
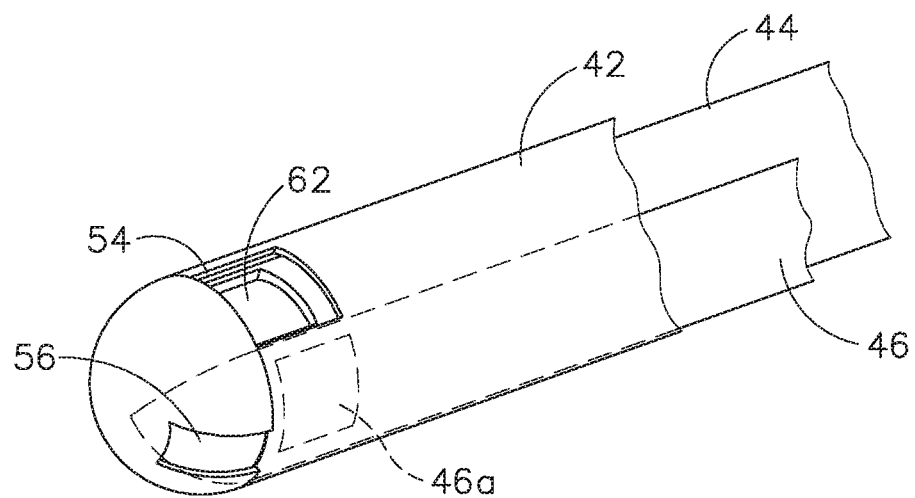
FIG. 6 depicts an enlarged perspective fragmentary view of the distal portion of the exemplary surgical cutting instrument of FIG. 1, with the shield in a second position.
Figure 7A:
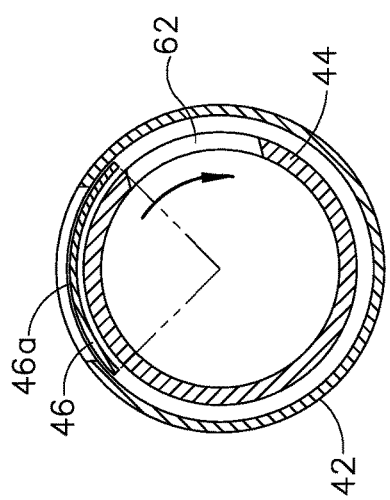
FIG. 7A depicts a cross-sectional view of the surgical cutting instrument of FIG. 1, taken at the position of line 7-7 of FIG. 3 when the shield is in the position illustrated in FIG. 5.
Figure 7B:
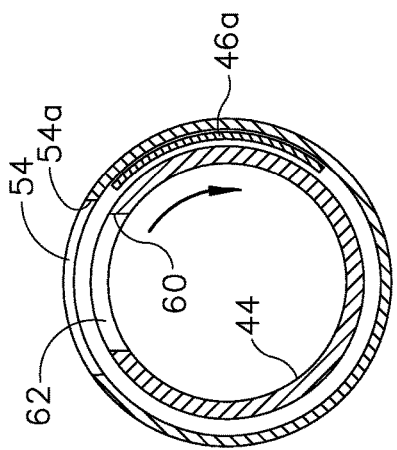
FIG. 7B depicts a cross-sectional view of the surgical cutting instrument of FIG. 1, taken at the position of line 7-7 of FIG. 3, when the shield is in the position illustrated in FIG. 6.

Referring also to FIGS. 5-6, shield member (46) includes first shield portion (46a) which is selectively disposable at a first position and a second position. In FIGS. 3, 5 and 7A, first shield portion (46a) is disposed at a first position at which first shield portion (46a) occludes first window region (54). When first window region (54) is occluded, first cutting window (62) cannot contact tissue, and thus cannot cut tissue at first window region (54). In FIGS. 6 and 7B, first shield portion (46a) is disposed at a second position at which first shield portion (46a) does not occlude first window region (54), permitting tissue to be addressed by first cutting edge (60) through first window region (54).

Figure 8A:
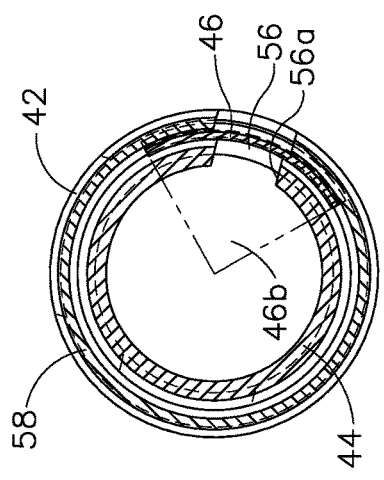
FIG. 8A depicts a cross-sectional view of the surgical cutting instrument of FIG. 1, taken at the position of line 8-8 of FIG. 3 when the shield is in the position illustrated in FIG. 5.
Figure 8B:
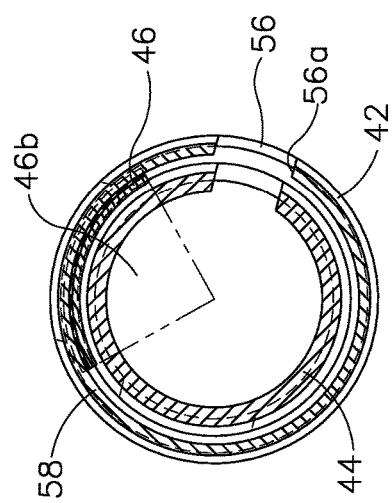
FIG. 8B depicts a cross-sectional view of the surgical cutting instrument of FIG. 1, taken at the position of line 8-8 of FIG. 3 when the shield is in the position illustrated in FIG. 6.

Shield member (46) includes second shield portion (46b) which is selectively disposable at a first position and a second position. In FIGS. 6 and 8B, second shield portion (46b) is disposed at a first position at which second shield portion (46b) occludes second window region (56). When second window region (56) is occluded, second cutting window (70) cannot contact tissue, and thus cannot cut tissue at second window region (56). In FIGS. 5 and 8A, second shield portion (46b) is disposed at a second position at which second shield portion (46b) does not occlude second window region (56), permitting tissue to be addressed by second cutting edge (68) through second window region (56). Second shield portion (46b) is illustrated as comprising at least a portion of curved segment (46b).

In this exemplary surgical cutting instrument, shield member (46) is configured such that when first shield portion (46a) is disposed at its first position, second shield portion (46b) is disposed at its second position, and such that when first shield portion (46a) is disposed at its second position, second shield portion (46b) is disposed at its first position. In this configuration, shield member (46) itself need only be moveable between and including its own first and second positions in order to selectively dispose first and second shield portions (46a, 46b) at their respective first and second positions. The positioning and movement of shield member (46) may be effected and controlled in any suitable manner. Shield member (46) may extend to hub (30) and connect with any suitably configured control feature. Various suitable features that may be used to drive and/or otherwise control shield member (46) will be apparent to those of ordinary skill in the art in view of the teachings herein.

In this exemplary surgical cutting instrument, first shield portion (46a) and second shield portion (46b) are axially aligned. First window region (54) and second window region (56) are axially offset an amount such that the axially aligned first shield portion (46a) is disposed at its first position when the second shield portion (46b) is disposed at its second position, and the first shield portion (46a) is disposed at its second position when the second shield portion (46b) is disposed at its first position.

During the cutting operation, shield portions (46a, 46b) need to be held in their desired respective positions so that an occluded window region place remains occluded and a non-occluded window region remains non-occluded through the operation. Shield member (46) is configured to be locked in respective positions to maintain shield portions (46a, 46b) at the desired positions. Various suitable features that may be used to selectively lock shield member (46) will be apparent to those of ordinary skill in the art in view of the teachings herein.

Either or both of first shield portion (46a) and second shield portion (46b) may be configured such that only a portion of a respective first and second window region (54, 56) is occluded by its respective shield portion (46a, 46b) whereby the size of the unoccluded portion of the respective window region (54, 56) may be determined by the position of the respective shield portion (46a, 46b), and thereby limit the amount of tissue that can be addressed by the respective cutting edge (60, 68) during one pass across the respective window region (54, 56). Corresponding portions of shield portion (46a, 46b) may be configured to act as an opposing surface to its respective cutting window (62, 68), and such configuration of the corresponding portions may be any suitable configuration, such as a knife edge, a serrated edge, bipolar, monopolar or harmonic energy modality, or laser activated cutting edge.

Figure 9:
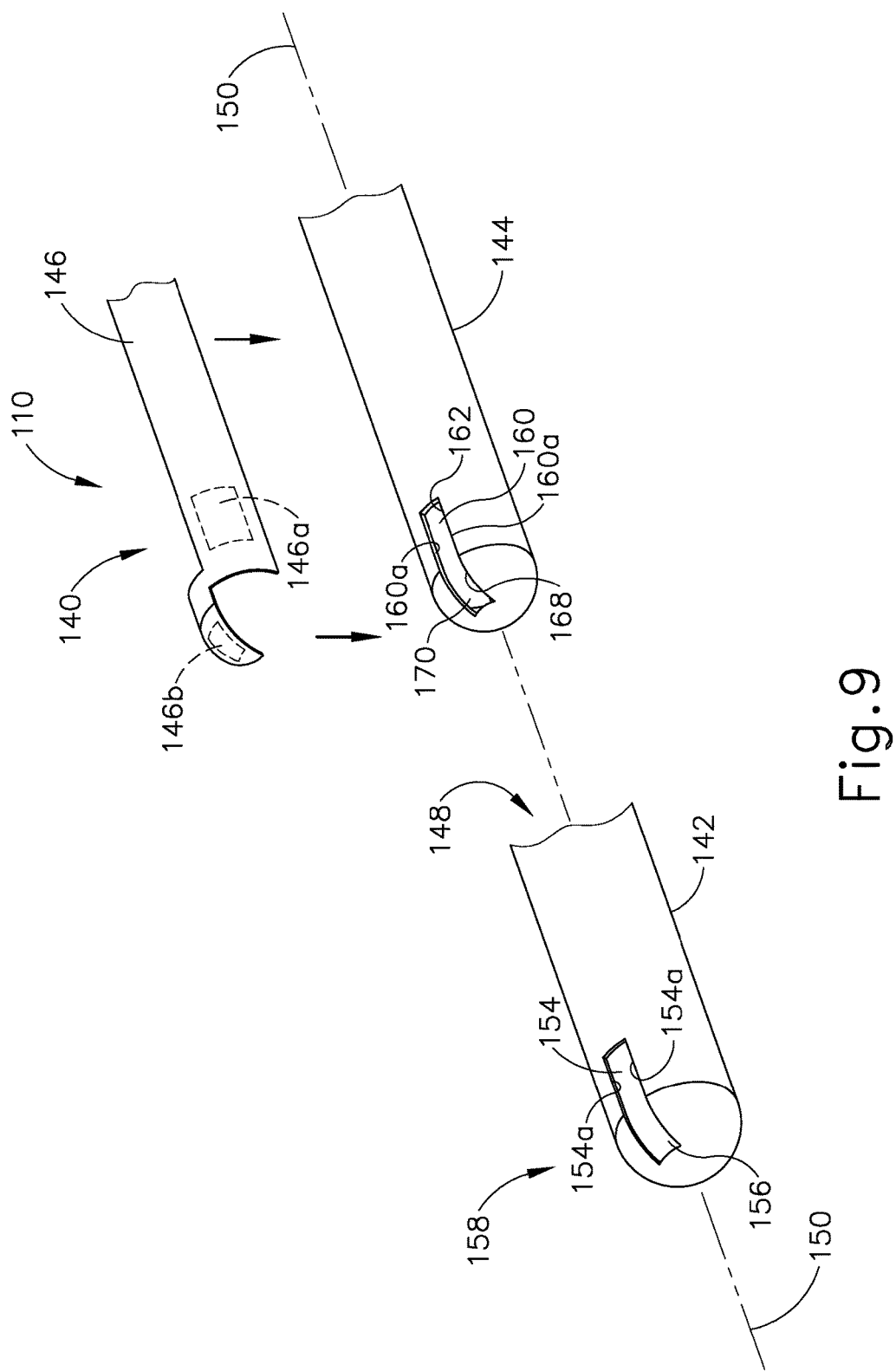
FIG. 9 depicts an exploded perspective fragmentary view of the distal portion of another exemplary surgical cutting instrument.

Movement of shield portions (46a, 46b) between and including their respective first and second positions may be effected in any suitable manner. As illustrated, rotation of shield member (46) about axis (50) effects the movement of first and second shield portions (46a, 46b) between and including their respective first and second positions. Shield member (46) may alternatively be configured for other movement in order to effect movement of first and second shield portions (46a, 46b) to and between their respective first and second positions, such as axial movement or a combination of axial and rotational. Alternatively, first and second shield portions (46a, 46b) may comprise separate members, moveable independently, inter-dependently or in unison to achieve a desired combination of occluded II. Exemplary Surgical Cutting Instrument with Adjacent Window Regions FIG. 9 depicts a distal portion of a shaft assembly (140) of another exemplary surgical cutting instrument (110). Shaft assembly (140) comprises shaft (142), cutting member (144) and shield (146). Shaft (142) includes first window region (154) and second window region (156). First window region (154) and second window region (156) are adjacent each other and are contiguous, being in communication with each other. First window region (154) and second window region (156) are axially aligned. First window region (154) opens toward a first direction, radially outwardly relative to longitudinal axis (150) such that tissue or bone may extend through first window region (154) into central lumen (148) in a radially inward direction when distal portion (158) is urged radially against such tissue or bone. Second window region (156) opens toward a second direction, axially (or parallel) relative to longitudinal axis (150) such that tissue or bone may extend through second window region (156) into central lumen (148) when distal portion (158) is urged axially against such tissue or bone. As above, it is noted that the second direction includes a radial directional component in addition to the axial directional component such that tissue or bone may extend through second window region (156) when distal portion (158) is urged radially against such tissue or bone. The second window region (156) may be located and oriented in any suitable direction, such as such that the second direction does not include a radial directional component or includes only a radial direction component. Shaft (142) may be made of any suitable material, such as polycarbonate.

Cutting member (144) may be made of any suitable material, such as stainless steel. Cutting member (144) includes first cutting edge (160) which defines first cutting window (162) at distal portion (164) of cutting member (144). Cutting member (144) includes second cutting edge (168) which defines second cutting window (170) at distal portion (164) of cutting member (144). First cutting window (162) and second cutting window (170) are adjacent each other and contiguous, being in communication with each other. First cutting edge (160) is disposed in lumen (148) and configured to be cyclically moved across at least a portion of first window region (154). Second cutting edge (168) is disposed in lumen (148) and configured to be cyclically moved across at least a portion of second window region (158). Edge (154a) is similar to edge (54a) and first cutting edge portion (160a) is similar to first cutting edge (54a).

Shield (146) includes first shield portion (146a) which is selectively disposable at a first position and a second position. When first shield portion (146a) is disposed at the first position, first shield portion (146a) occludes first window region (154). When first window region (154) is occluded, first cutting window (162) cannot contact tissue, and thus cannot cut tissue at first window region (154). When first shield portion (146a) is disposed at the second position, first shield portion (146a) does not occlude first window region (154), permitting tissue to be addressed by first cutting edge (160) through first window region (154).

Shield (146) includes second shield portion (146b) which is selectively disposable at a first position and a second position. When second shield portion (146b) is disposed at the first position, second shield portion (146b) occludes second window region (156). When second window region (156) is occluded, second cutting window (170) cannot contact tissue, and thus cannot cut tissue at second window region (156). When second shield portion (146b) is disposed at the second position, second shield portion (146b) does not occlude second window region (156), permitting tissue to be addressed by second cutting edge (168) through second window region (156).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a shaft, wherein the shaft comprises a longitudinal axis, wherein the shaft defines a lumen, wherein the shaft comprises a distal portion and a proximal portion, wherein the shaft comprises a first window region and a second window region; (b) a first cutting edge disposed in said lumen, wherein the first cutting edge is configured to be cyclically moved across at least a portion of the first window region; (c) a second cutting edge disposed in said lumen, wherein the second cutting edge is configured to be cyclically moved across at least a portion of the second window region; (d) a first shield portion which is selectively disposable at a first position and at a second position, wherein the first shield portion is configured to occlude the first window region when the first shield portion is disposed at the first position; wherein the first shield portion is configured to not occlude the first window region when the first shield portion is disposed at the second position; and (e) a second shield portion which is selectively disposable at a third position and at a fourth position, wherein the second shield portion is configured to occlude the second window region when the second shield portion is disposed at the third position; wherein the second shield portion is configured to not occlude the second window region when the second shield portion is disposed at the fourth position.

Example 2

The apparatus of Example 1, wherein the first window region and the second window region are contiguous.

Example 3

The apparatus of Example 2, wherein the first window region and the second window region are axially aligned.

Example 4

The apparatus of any one or more of Examples 1 through 3, wherein the first window region is disposed in the distal portion.

Example 5

The apparatus of Example 4, wherein the distal portion comprises a curved end, and wherein the second window region is disposed in the curved end.

Example 6

The apparatus of any one or more of Examples 1 through 5, wherein the first window region is oriented toward a first direction, wherein the first direction comprises a radial directional component relative to the longitudinal axis.

Example 7

The apparatus of Example 6, wherein the first direction comprises only the radial directional component.

Example 8

The apparatus of any one or more of Examples 6 through 7, wherein the second window region is oriented toward a second direction, wherein the second direction comprises an axial directional component relative to the longitudinal axis.

Example 9

The apparatus of any one or more of Examples 1 through 8, wherein the first window region is oriented toward a first direction, wherein the first direction comprises only an axial directional component relative to the longitudinal axis.

Example 10

The apparatus of any one or more of Examples 1 through 9, comprising a cutting member, wherein the cutting blade comprises the first cutting edge.

Example 11

The apparatus of Example 10, wherein the cutting member comprises the second cutting edge.

Example 12

The apparatus of any one or more of Examples 1 through 11, comprising a shield member, wherein the shield comprises the first shield portion and the second shield portion.

Example 13

The apparatus of Example 12, wherein the first shield portion and the second shield portion are axially aligned.

Example 14

The apparatus of any one or more of Examples 12 through 13, wherein the shield member comprises a curved segment and wherein said second shield portion is disposed at the curved segment.

Example 15

The apparatus of any one or more of Examples 12 through 4, wherein the shield member comprises a cylindraceous sector.

Example 16

The apparatus of any one or more of Examples 1 through 15, wherein the first shield portion is disposed in the lumen.

Example 17

The apparatus of Example 16, wherein the second shield portion is disposed in the lumen.

Example 18

An apparatus comprising: (a) a shaft, wherein the shaft comprises a longitudinal axis; wherein the shaft defines a first lumen, wherein the shaft comprises a distal portion and a proximal portion, wherein the shaft comprises a first window region and a second window region, wherein the first window region is oriented toward a first direction which comprises only a radial directional component; wherein the second window region is oriented toward a second direction which comprises an axial directional component; (b) a cutting member disposed in the first lumen, wherein the cutting member comprises a second lumen, wherein the cutting member comprises a first cutting edge disposed in said lumen, wherein the first cutting edge is configured to be cyclically moved across at least a portion of the first window region, wherein the cutting member comprises a second cutting edge, wherein the second cutting edge is configured to be cyclically moved across at least a portion of the second window region; and (c) a shield member which is selectively disposable at a first position and at a second position, wherein the shield member is configured to occlude the first window region and not to occlude the second window region when the shield member is disposed at the first position; wherein the shield member is configured not to occlude the first window region and to occlude the second window region when the shield member is disposed at the second position.

Example 19

The apparatus of Example 18, comprising a suction port in fluid communication with the second lumen.

Example 20

An apparatus comprising: (a) a handle assembly comprising (i) a distal end and a proximal end; (ii) a suction port which is connectable to a vacuum source; and (iii) a rotary or oscillatory motion source; and (b) a shaft assembly comprising: (i) a shaft, wherein the shaft comprises a longitudinal axis, wherein the shaft defines a lumen, wherein the shaft comprises a distal portion and a proximal portion, wherein the proximal portion of the shaft is connected to the distal end of the handle assembly, wherein the shaft comprises a first window region and a second window region; (ii) a cutting member disposed in the first lumen, wherein the rotary or oscillatory motion source is configured to rotate the cutting member about the longitudinal axis, wherein the cutting member comprises a second lumen which is in fluid communication with the suction port, wherein the cutting member comprises a first cutting edge configured to be cyclically moved across at least a portion of the first window region, wherein the cutting member comprises a second cutting edge configured to be cyclically moved across at least a portion of the second window region; and (iii) a shield member which is selectively disposable at a first position and at a second position, wherein the shield member is configured to occlude the first window region and not to occlude the second window region when the shield member is disposed at the first position; wherein the shield member is configured not to occlude the first window region and to occlude the second window region when the shield member is disposed at the second position.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a shaft, wherein the shaft comprises a longitudinal axis, wherein the shaft defines a lumen, wherein the shaft comprises a distal portion and a proximal portion, wherein the shaft comprises a first window region and a second window region;
   (b) a first cutting edge disposed in said lumen and extending along a portion of the longitudinal axis, wherein the first cutting edge is configured to be cyclically moved across at least a portion of the first window region;
   (c) a second cutting edge disposed in said lumen, wherein the second cutting edge is configured to be cyclically moved across at least a portion of the second window region;
   (d) a first shield portion which is selectively rotatable relative to the shaft and the first cutting edge between a first position and a second position, wherein the first shield portion is configured to occlude the first window region when the first shield portion is rotated to the first position, wherein the first shield portion is configured to not occlude the first window region when the first shield portion is rotated to the second position; and
   (e) a second shield portion which is selectively rotatable relative to the shaft and the second cutting edge between a third position and a fourth position, wherein the second shield portion is configured to occlude the second window region when the second shield portion is rotated to the third position, wherein the second shield portion is configured to not occlude the second window region when the second shield portion is rotated to the fourth position.

2. The apparatus of claim 1, wherein the first window region and the second window region are contiguous.

3. The apparatus of claim 2, wherein the first window region and the second window region are axially aligned.

4. The apparatus of claim 1, wherein the first window region is disposed in the distal portion.

5. The apparatus of claim 4, wherein the distal portion comprises a curved end, and wherein the second window region is disposed in the curved end.

6. The apparatus of claim 1, wherein the first window region is oriented toward a first direction, wherein the first direction comprises a radial directional component relative to the longitudinal axis.

7. The apparatus of claim 6, wherein the first direction comprises only the radial directional component.

8. The apparatus of claim 6, wherein the second window region is oriented toward a second direction, wherein the second direction comprises an axial directional component relative to the longitudinal axis.

9. The apparatus of claim 1, wherein the first window region is oriented toward a first direction, wherein the first direction comprises only an axial directional component relative to the longitudinal axis.

10. The apparatus of claim 1, comprising a cutting member, wherein the cutting blade comprises the first cutting edge.

11. The apparatus of claim 10, wherein the cutting member comprises the second cutting edge.

12. The apparatus of claim 1, comprising a shield member, wherein the shield member comprises the first shield portion and the second shield portion.

13. The apparatus of claim 12, wherein the first shield portion and the second shield portion are axially aligned.

14. The apparatus of claim 12, wherein the shield member comprises a curved segment and wherein said second shield portion is disposed at the curved segment.

15. The apparatus of claim 12, wherein the shield member comprises a cylindraceous sector.

16. The apparatus of claim 1, wherein the first shield portion is disposed in the lumen.

17. The apparatus of claim 16, wherein the second shield portion is disposed in the lumen.

18. An apparatus comprising:
   (a) a shaft, wherein the shaft comprises a longitudinal axis, wherein the shaft defines a first lumen, wherein the shaft comprises a distal portion and a proximal portion, wherein the shaft comprises a first window region and a second window region, wherein the first window region is oriented toward a first direction which comprises only a radial directional component, wherein the second window region is oriented toward a second direction which comprises an axial directional component;
   (b) a cutting member disposed in the first lumen, wherein the cutting member comprises a second lumen, wherein the cutting member comprises a first cutting edge disposed in said lumen, wherein the first cutting edge is configured to be cyclically rotated across at least a portion of the first window region, wherein the cutting member comprises a second cutting edge, wherein the second cutting edge is configured to be cyclically moved across at least a portion of the second window region; and
   (c) a shield member which is selectively rotatable relative to the shaft and the cutting member between a first position and a second position, wherein the shield member is configured to occlude the first window region and not to occlude the second window region when the shield member is rotated to the first position, wherein the shield member is configured not to occlude the first window region and to occlude the second window region when the shield member is rotated to the second position.

19. The apparatus of claim 18, comprising a suction port in fluid communication with the second lumen.

20. An apparatus comprising:
   (a) a handle assembly comprising
      (i) a distal end and a proximal end; and
      (ii) a suction port which is connectable to a vacuum source;
   (b) a shaft assembly comprising:
      (i) a shaft, wherein the shaft comprises a longitudinal axis, wherein the shaft defines a lumen, wherein the shaft comprises a distal portion and a proximal portion, wherein the proximal portion of the shaft is connected to the distal end of the handle assembly, wherein the shaft comprises a first window region and a second window region;
      (ii) a cutting member disposed in the first lumen, wherein the cutting member is configured to rotate about the longitudinal axis, wherein the cutting member comprises a second lumen which is in fluid communication with the suction port, wherein the cutting member comprises a first cutting edge configured to be cyclically moved across at least a portion of the first window region, wherein the cutting member comprises a second cutting edge configured to be cyclically moved across at least a portion of the second window region; and
      (iii) a shield member which is selectively rotatable relative to the shaft and the cutting member between a first position and a second position, wherein the shield member is configured to occlude the first window region and not to occlude the second window region when the shield member is rotated to the first position; wherein the shield member is configured not to occlude the first window region and to occlude the second window region when the shield member is rotated to the second position.

* * * * *